US009354159B2

(12) United States Patent
Vaartstra

(10) Patent No.: US 9,354,159 B2
(45) Date of Patent: May 31, 2016

(54) OPTO-FLUIDIC SYSTEM WITH COATED FLUID CHANNELS

(71) Applicant: NANOSCOPIA (CAYMAN), INC., Grand Cayman (CY)

(72) Inventor: Brian Vaartstra, Nampa, ID (US)

(73) Assignee: NanoScopia (Cayman), Inc., Grand Cayman (KY)

( * ) Notice: Subject to any disclaimer, the term of this patent is extended or adjusted under 35 U.S.C. 154(b) by 331 days.

(21) Appl. No.: 13/875,595

(22) Filed: May 2, 2013

(65) Prior Publication Data

US 2013/0307954 A1    Nov. 21, 2013

Related U.S. Application Data

(60) Provisional application No. 61/641,806, filed on May 2, 2012.

(51) Int. Cl.
*H01L 27/146* (2006.01)
*G01N 21/75* (2006.01)
*G01N 21/01* (2006.01)
(Continued)

(52) U.S. Cl.
CPC ............ *G01N 21/01* (2013.01); *G01N 21/6454* (2013.01); *H01L 27/14603* (2013.01); *H04N 7/18* (2013.01); *Y10T 156/10* (2015.01)

(58) Field of Classification Search
CPC ............. H01L 27/14603; G01N 21/01; G01N 21/6454; H04N 7/18; Y10T 156/10
See application file for complete search history.

(56) References Cited

U.S. PATENT DOCUMENTS 5,411,876 A    5/1995    Bloch et al.
5,498,392 A    3/1996    Wilding et al.
(Continued)

FOREIGN PATENT DOCUMENTS

EP    1442787 A2    8/2004
EP    2258951 A1    12/2010
(Continued)

OTHER PUBLICATIONS

Cui et al., "Lensless high-resolution on-chip optofluidic microscopes for Caehorhabditis elegans and cell imaging" [online], May 2008 [retrieved on May 11, 2011]. Retrieved from the Internet: http://www.biophot.caltech.edu/publications/pdf/2008-OFM-PNAS.pdf.
(Continued)

*Primary Examiner* — Nikolay Yushin
(74) *Attorney, Agent, or Firm* — Shay Glenn LLP

(57) ABSTRACT

An image sensor integrated circuit may contain image sensor pixels. A channel for receiving a fluid with samples may be formed on top of the image sensor. The image sensor pixels may form light sensors and imagers. The imagers may gather images of the samples as the fluid passes over the imagers or when the samples from the fluid adhere to the surface above an imager array. A protective coating may be formed on surfaces of the channel to protect the image sensor pixels and integrated circuit from potentially damaging materials in the fluid, samples, or materials provided for evaluating the samples. The protective coating may be a base-resistant material such as a silylating agent. A cover glass may be attached above the image sensor integrated circuit to form a portion of the channel. The protective coating may be formed on surfaces of the cover glass.

18 Claims, 3 Drawing Sheets

(51) Int. Cl.
*H04N 7/18* (2006.01)
*G01N 21/64* (2006.01)

(56) References Cited

U.S. PATENT DOCUMENTS

| | | | |
|---|---|---|---|
| 5,753,186 | A | 5/1998 | Hanley et al. |
| 6,132,685 | A | 10/2000 | Kercso et al. |
| 6,326,083 | B1 * | 12/2001 | Yang .................. A61L 31/10 427/2.25 |
| 6,379,929 | B1 | 4/2002 | Burns et al. |
| 6,456,754 | B1 | 9/2002 | Augustsson |
| 6,630,205 | B2 * | 10/2003 | Brueck ................ C08G 77/22 427/387 |
| 6,723,290 | B1 | 4/2004 | Wardlaw |
| 6,866,823 | B2 | 3/2005 | Wardlaw |
| 7,348,969 | B2 | 3/2008 | Robrecht et al. |
| 7,391,053 | B2 | 6/2008 | Iizuka et al. |
| 7,435,578 | B2 | 10/2008 | Wikswo et al. |
| 7,452,726 | B2 | 11/2008 | Chou et al. |
| 7,466,409 | B2 | 12/2008 | Scherer et al. |
| 7,492,167 | B2 | 2/2009 | Reich et al. |
| 7,524,459 | B2 | 4/2009 | Adams et al. |
| 7,695,683 | B2 | 4/2010 | Quan et al. |
| 7,751,048 | B2 | 7/2010 | Yang et al. |
| 7,863,035 | B2 | 1/2011 | Clemens et al. |
| 7,868,665 | B2 | 1/2011 | Tumer et al. |
| 8,105,849 | B2 | 1/2012 | Mcdevitt et al. |
| 8,314,933 | B2 | 11/2012 | Cui et al. |
| 8,465,698 | B2 | 6/2013 | Yamakawa et al. |
| 8,717,556 | B2 | 5/2014 | Salsman |
| 8,794,050 | B2 | 8/2014 | Hutto et al. |
| 8,911,941 | B2 | 12/2014 | Michlitsch |
| 2002/0081716 | A1 | 6/2002 | Yagi |
| 2003/0013109 | A1 | 1/2003 | Ballinger et al. |
| 2003/0138819 | A1 | 7/2003 | Gong et al. |
| 2004/0115731 | A1 | 6/2004 | Hansen et al. |
| 2004/0151629 | A1 | 8/2004 | Pease et al. |
| 2004/0165778 | A1 | 8/2004 | Cartlidge et al. |
| 2004/0191119 | A1 | 9/2004 | Zanzucchi et al. |
| 2005/0106713 | A1 | 5/2005 | Phan et al. |
| 2005/0271548 | A1 | 12/2005 | Yang et al. |
| 2007/0003443 | A1 | 1/2007 | Sandell et al. |
| 2007/0141605 | A1 | 6/2007 | Vann et al. |
| 2007/0292858 | A1 | 12/2007 | Chen et al. |
| 2007/0292941 | A1 | 12/2007 | Handique et al. |
| 2008/0176755 | A1 | 7/2008 | Amundson et al. |
| 2008/0280285 | A1 | 11/2008 | Chen et al. |
| 2009/0130745 | A1 | 5/2009 | Williams et al. |
| 2009/0147918 | A1 | 6/2009 | Fowler et al. |
| 2009/0325276 | A1 | 12/2009 | Battrell et al. |
| 2010/0015621 | A1 | 1/2010 | Chang et al. |
| 2010/0054574 | A1 | 3/2010 | Marcelpoil et al. |
| 2010/0079408 | A1 | 4/2010 | Leong et al. |
| 2010/0186524 | A1 | 7/2010 | Ariessohn et al. |
| 2010/0296094 | A1 | 11/2010 | Yang et al. |
| 2011/0170105 | A1 * | 7/2011 | Cui .................. G02B 21/33 356/450 |
| 2011/0234757 | A1 | 9/2011 | Zheng et al. |
| 2011/0294112 | A1 | 12/2011 | Bearinger et al. |
| 2011/0294199 | A1 | 12/2011 | Bearinger et al. |
| 2011/0311394 | A1 | 12/2011 | Worsman et al. |
| 2012/0008848 | A1 | 1/2012 | Beck |
| 2012/0044339 | A1 | 2/2012 | Stith et al. |
| 2012/0045103 | A1 * | 2/2012 | Salsman ............ G01N 15/1012 382/128 |
| 2012/0045787 | A1 | 2/2012 | Boettiger |
| 2012/0202211 | A1 | 8/2012 | Ochoa Corona |
| 2012/0218379 | A1 | 8/2012 | Ozcan et al. |
| 2012/0250027 | A1 | 10/2012 | Zheng et al. |
| 2012/0329142 | A1 | 12/2012 | Battrell et al. |
| 2014/0356874 | A1 | 12/2014 | Bearinger et al. |
| 2015/0035966 | A1 | 2/2015 | Salsman |
| 2015/0036131 | A1 | 2/2015 | Salsman |
| 2015/0037786 | A1 | 2/2015 | Salsman |
| 2015/0300957 | A1 | 10/2015 | Salsman |

FOREIGN PATENT DOCUMENTS

| | | |
|---|---|---|
| WO | WO2009/018473 A1 | 2/2009 |
| WO | WO2009/111573 A2 | 9/2009 |
| WO | WO2011/073410 A1 | 6/2011 |
| WO | WO2012/068499 A2 | 5/2012 |

OTHER PUBLICATIONS

Cui et al., "Quantitative differential interference contrast microscopy based on structured-aperture interference" [online], Sep. 2008 [retrieved on May 11, 2011]. Retrieved from the Internet: http://www.biophot.caltech.edu/publications/pdf/Cui-APL-2007-DIC.pdf.

Wu et al., "The application of Fresnel zone plate based projection in optofluidic microscopy" [online], Sep. 2008 [retrieved on May 11, 2011]. Retrieved from the Internet: http://www.biophot.caltech.edu/publications/pdf/Wu-OE-2008-Fresnel.pdf.

Stith et al., U.S. Appl. No. 13/205,340, filed Aug. 8, 2011.

Salsman et al., U.S. Appl. No. 13/114,982, filed May 24, 2011.

Stith et al., U.S. Appl. No. 13/114,990, filed May 24, 2011.

Bearinger et al.; Development and initial results of a low cost, disposable, point-of-care testing device for pathogen detection; IEEE Trans on Biomedical Engineering; 58(3); pp. 805-808; Mar. 2011.

Good et al.; An effervescent reaction micropump for portable microfluidic systems; Lab on a Chip; Royal Society of Chemistry; 6(5); pp. 659-666; May 2006.

Hart et al.; Point-of-care oral-based diagnostics; Oral Diseases; 17(8); pp. 745-752; Nov. 2011.

Jacoby; Chromatograpy in the extreme; Chemical & Engineering News; 86(17); pp. 17-23; Apr. 28, 2008 (retrieved Nov. 9, 2015 from the internet: http://cen.acs.org/articles/86/i17/Chromatography-Extreme.html: 5 pgs.).

Jangam et al.; Rapid, point-of-care extraction of himan immunodeficiency virus type 1 proviral DNA from whole blood for detection by real time PCR; Journal of Clinical Microbiology; 47(8); pp. 2363-2368; Aug. 2009.

LaBarre et al.; Non-instrumented nucleic acid amplification (NINA): Instrument free molecular malaria diagnostics for low-resource settings; 32nd Ann. Int. Conf. of the IEEE EMBS; Buenos Aires, Argentina; pp. 1097-1099; Aug. 31-Sep. 4, 2010.

Menassa et al.; Rapid detection of fungal keratitis with DNA-stabilizing FTA filter paper; Investigative Ophthalmology & Visual Science; 51(4); pp. 1905-1910; Apr. 2010.

Pang et al.; Fluorescence microscopy imaging with a Fresnel zone plate array based optofluidic microscope; Lab on a Chip; 11; pp. 3698-3702; Nov. 2011.

Poon et al.; Sensitive and inexpensive molecular test for falciparum malaria: Detecting plamodium falciparum DNA directly for heat-treated blood by loop-mediated isothermal amplification; Clinical Chemistry; 52(2); pp. 303-306; Dec. 2006.

Weigl et al.; Non-instrumented nucleic-acid amplification assay; Microfluidics; BioMEMS, and Medical Microsystems VI; Proc. of SPIE; 6886(04); San Jose, CA; 12 pgs.; Jan. 19, 2008.

* cited by examiner

OPTO-FLUIDIC SYSTEM WITH COATED FLUID CHANNELS

This application claims the benefit of provisional patent application No. 61/641,806, filed May 2, 2012 which is hereby incorporated by reference herein in its entirety.

BACKGROUND

This relates generally to near-field sensor systems such as opto-fluidic systems, and, more particularly, to using such systems to image and evaluate fluid samples containing cells and other specimens.

Opto-fluidic sensors have been developed that can be used to generate images of cells and other biological samples. In conventional systems, the samples are suspended in a fluid. The fluid flows over a set of image sensor pixels in a channel. The image sensor pixels may be associated with an image sensor pixel array. As the fluid flows through the channel, image data from the pixels may be acquired and processed to form high-resolution images of the sample.

Chemicals such as reactants and reagents may be included in the channel or in the fluid for interacting with the samples. If care is not taken, these types of chemicals can damage portions of the system.

It would therefore be desirable to provide improved microfluidic imaging systems.

DETAILED DESCRIPTION

Figure 1:
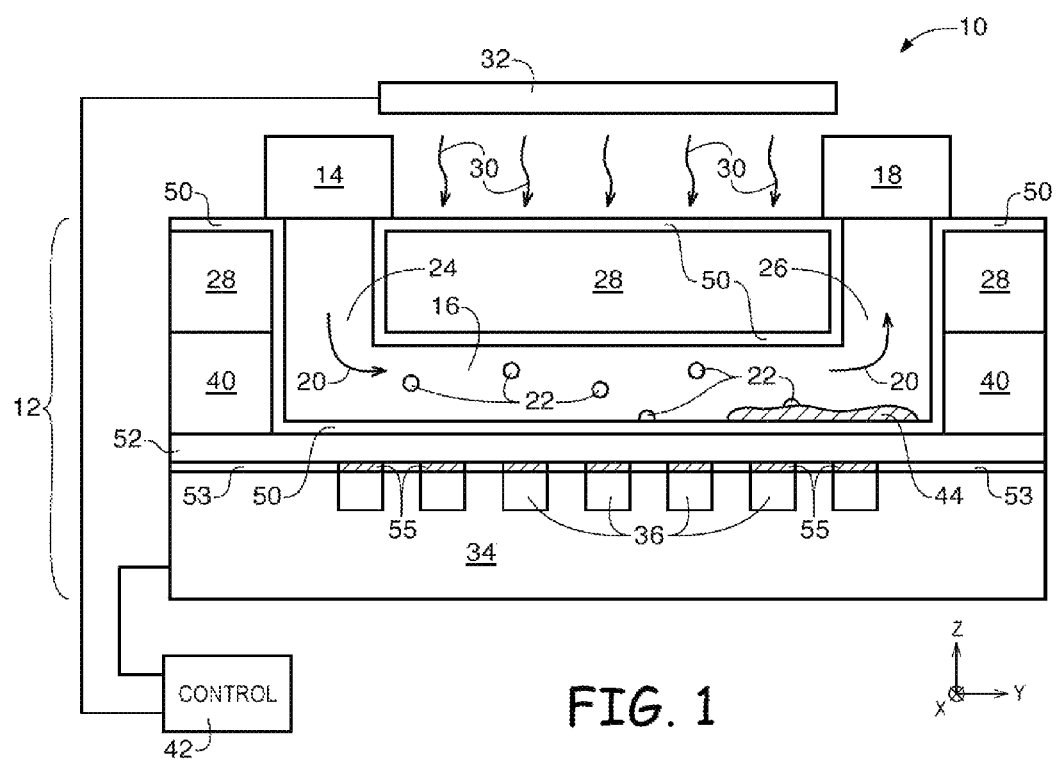
FIG. 1 is a diagram of an illustrative system for imaging and evaluating samples in accordance with an embodiment of the present invention.

A system of the type that may be used to image and otherwise evaluate cells and other samples such as biological specimens is shown in FIG. 1. As shown in FIG. 1, system 10 may include opto-fluidic sensor 12. Sensor 12 may include an image sensor integrated circuit such as image sensor integrated circuit 34. Image sensor integrated circuit 34 may be formed from a semiconductor substrate material such as silicon and may contain numerous image sensor pixels 36. Complementary metal-oxide-semiconductor (CMOS) technology or other image sensor integrated circuit technologies may be used in forming image sensor pixels 36 and integrated circuit 34.

Image sensor pixels 36 may form part of an array of image sensor pixels on image sensor integrated circuit 34 (e.g., a rectangular array). Some of the pixels may be actively used for gathering light. Other pixels may be inactive or may be omitted from the array during fabrication. In arrays in which fabricated pixels are to remain inactive, the inactive pixels may be covered with metal or other opaque materials, may be depowered, or may otherwise be inactivated. There may be any suitable number of pixels fabricated in integrated circuit 34 (e.g., tens, hundreds, thousands, millions, etc.). The number of active pixels in integrated circuit 34 may be tens, hundreds, thousands, or more).

Image sensor integrated circuit 34 may be covered with a transparent layer of material such as glass layer 28 or other covering layers. Layer 28 (sometimes referred to as cover glass 28) may, if desired, be colored or covered with filter coatings (e.g., coatings of one or more different colors to filter light). Structures such as bond layer 40 (e.g., polymer standoffs) may be used to elevate the lower surface of glass layer 28 from the upper surface of image sensor integrated circuit 34. This forms one or more channels such as channels 16. Channels 16 may have lateral dimensions (dimensions parallel to dimensions x and z in the example of FIG. 1) of a millimeter or less (as an example). The length of each channel (the dimension of channel 16 along dimension y in the example of FIG. 1) may be 1-10 mm, less than 10 mm, more than 10 mm, may encompass the entire pixel array, or even areas outside of the array. Bond layer 40 may be patterned to form sidewalls for channels such as channel 16.

During operation, fluid flows through channel 16 as illustrated by arrows 20. A fluid source such as fluid source 14 may be used to introduce fluid into channel 16 through entrance port 24. Fluid 14 may, for example, be dispensed from a pipette, from a drop on top of port 24, from a fluid-filled reservoir, from tubing that is coupled to an external pump, etc. Fluid 14 may exit channel 16 through exit port 26 and may, if desired, be collected in a reservoir 18. Reservoirs (sometimes referred to as chambers) may also be formed within portions of channel 16.

The rate at which fluid flows through channel 16 may be controlled using fluid flow rate control structures. Examples of fluid flow rate control structures that may be used in system 10 include pumps, electrodes, microelectromechanical systems (MEMS) devices, etc. If desired, structures such as these (e.g., MEMs structures or patterns of electrodes) may be used to form fluid flow control gates (i.e., structures that selectively block fluid flow or allow fluid to pass and/or that route fluid flow in particular directions). For example, channel 16 may be provided with one or more electrodes. By controlling the voltage applied across the electrodes, the flow rate of fluids in channel 16 such as ionic fluids may be controlled by control circuitry 42.

Fluid 14 may contain samples such as samples 22. Samples 22 may be cells, proteins, DNA, reagents, fluorescent species, or other biological or chemical agents or particles. In one application of the device, as samples 22 pass by sensor pixels 36, image data may be acquired. In effect the cells are "scanned" across the pattern of sensor pixels 36 in channel 16 in much the same way that a printed image is scanned in a fax machine. Control circuitry 42 (which may be implemented as external circuitry or as circuitry that is embedded within image sensor integrated circuit 34) may be used to process the image data that is acquired using sensor pixels 36. Because the size of each image sensor pixel 36 is typically small (e.g., on the order of 0.5-5.6 microns or less in width), precise image data may be acquired. This allows high-resolution images of samples 22 to be produced. A typical cell may have dimensions on the order of 1-10 microns (as an example). Images of other samples (e.g., other biological specimens) may also be acquired in this way. Arrangements in which cells are imaged are sometimes described herein as an example.

In another application of the device, sample 22 may be chemisorbed or physisorbed to the surface directly above the pixel array. Light source 32 may be used to illuminate the sample for capturing static images of the sample or light source 32 may generate light of a specific wavelength that causes fluorescent molecules in the sample to emit light or other energy (e.g. infrared radiation) of a known wavelength. In a suitable example, sample 22 may contain DNA strands that are chemisorbed to the sensor surface via additional intermediate bonding molecules. Sample 22 may have fluorescent marker molecules attached to the opposite end of the strands. Sensor 12 may capture images of the fluorescent light from the fluorescent marker molecules and generate measurement data such as the intensity of fluorescence and location of the fluorescent molecules.

Pixels 36 may be configured to selectively bond to portions of sample 22. For example, fluorescent marker molecules may be attached to some DNA or protein strands in sample 22. As the sample flows through channel 16, DNA or protein strands with fluorescent marker molecules in sample 22 may selectively bond to sites on the sensor array such as pixels 36. Image data of sample 22 from pixels 36 may be acquired and processed to form high-resolution images of the sample. Image sensor 34 may gather images of cells, fluorescent molecules, or other particles in sample 22 or fluid 14 as the fluid passes over the imagers. Alternatively, image sensor 34 may gather images of the sample after the fluid has passed over the image sensor and certain biological samples from the fluid have adhered to the surface above the pixel array.

During imaging operations, control circuit 42 (e.g., on-chip and/or off-chip control circuitry) may be used to control the operation of light source 32. Light source 32 may be based on one or more lamps, light-emitting diodes, lasers, or other sources of light. Light source 32 may be a white light source or may contain one or more light-generating elements 32-1, 32-2, 32-3 . . . 32-N that emit different colors of light. For example, light source 32 may contain multiple light-emitting diodes of different colors or may contain white light light-emitting diodes or other white light sources that are provided with different respective colored filters. Light source 32 may be configured to emit laser light of a desired frequency or combination of frequencies. If desired, layer 28 may be provided with colored transparent material in one or more regions that serve as one or more color filters. In response to control signals from control circuitry 42, light source 32 may produce light 30 of a desired color and intensity. Light 30 may pass through glass layer 28 to illuminate the sample in channel 16.

Pixels 36 may be arranged in a diagonal line that extends across the width of channel 16 or may be arranged in other suitable patterns. The use of a diagonal set of image acquisition pixels 36 in channel 16 may help improve resolution by increasing the number of pixels 36 per unit length in dimension x. The image acquisition pixels 36 in channel 16 (i.e., the imager sensor pixels) are sometimes referred to as forming an image acquisition region, image sensor, or imager.

Light source 32 may be adjusted to produce one or more different colors of light during image acquisition operations. Channel 16 in system 10 may be provided with one or more imagers 34. The different colors of light may be used in gathering image data in different color channels. A different light color may be used in illuminating samples 22 as samples 22 pass respective imagers 34 in channel 16 by moving in direction 20 with the fluid in channel 16.

In some situations, it may be desirable to mix fluid 14 and/or samples 22 with a reactant. Examples of reactants that may be introduced into channel 16 with fluid 14 and samples 22 include diluents (e.g., fluids such as ionic fluids), dyes (e.g., fluorescent dyes) or other chemical compounds, biological agents such as antigens, antibodies (e.g., antibodies with dye), etc. With one suitable arrangement, one or more reactants may be introduced within a portion of channel 16. The portion of channel 16 that receives the reactant may be, for example, a portion of channel 16 that has been widened or a portion of channel 16 that has the same width as the rest of the channel. Portions of channel 16 (whether widened or having other shapes) that receive reactant or that may be used to introduce sample material into channel 16 are sometimes referred to herein as chambers.

Some or all of channel 16 may be provided with reactant such as reactant 44 and/or components for evaluating samples such as samples 22. As shown in FIG. 1, for example, reactant 44 such as a fluorescent dye or other reactant may cover a portion of the lower surface of channel 16. This is merely illustrative. If desired, some or all of other surfaces such as the upper surface of channel 16 may be provided with reactant 44. Reactant 44 may be formed on or near the image sensor pixels 36 in channel 16 and/or in widened chambers within channel 16 (as examples). When fluid and samples 22 are introduced into chamber 16, reactant 62 may react with the fluid and/or samples.

In order to protect the structures of opto-fluidic sensor 12 such as channel 16 from potentially damaging materials in fluid 14 or in reactant 44, channel 16 may be provided with a protective coating such as passivation layer 50. Passivation layer 50 may be formed over some or all of the surfaces of channel 16 that may come into contact with fluid or reactants. For example, passivation layer 50 may be formed on some or all surfaces of cover glass 28. Passivation layer 50 may also be formed on the bottom surface of channel 16, on sidewall surfaces of channel 16, or within widened chambers in channel 16. Portions of bond layer 40 that are formed within channel 16 may be covered with passivation layer 50.

A barrier layer such as barrier layer 52 may be interposed between sensor pixels 36 and passivation layer 50. Barrier layer 52 may be formed from a transparent material such as an oxide material (e.g., silicon oxide) or other materials such as silicon nitride. During manufacturing and assembly operations, a sensor such as image sensor substrate 34 with a barrier layer may be obtained. Additional layers such as bond layer 40, protective layer 50, and cover glass layer 28 may then be formed on the obtained sensor.

If desired, system 10 may be provided with a color filter layer such as color filter layer 53. Color filter layer may be interposed between barrier layer 52 and substrate 34. Color filter layer 53 may include individual color filter elements 55 associated with each image pixel 36. Color filter elements 55 may be red color filter elements (e.g., photoresistive material that passes red light and blocks other colors of light from passing), blue color filter elements, green color filter elements, infrared color filter elements, or other color filter elements.

Passivation layer 50 may be formed from materials such as base-resistant materials, acid-resistant materials, or other protective materials that prevent damage to system 10 from fluids used in sample preparations such as alkaline solutions. In one suitable example, layer 50 may be formed from a base-resistant coating that protects surfaces of channel 16 from basic substances introduced by fluid 14. Passivation layer 50 may be formed from silylating agents having both inorganic and organic components. For example, passivation layer 50 may have a silicon oxide framework with numerous hydrocarbyl linkages that impart resistance to basic solutions, including solutions having a pH up to 12.

Passivation layer 50 may be bonded to some or all surfaces of channel 16 via chemisorption or physisorption. In chemisorption, passivation layer 50 may be chemically bonded to a surface of channel 16 by altering its electron structure to form chemical interactions such as covalent and ionic bonds. In physisorption, passivation layer 50 may be physically bonded to a surface of channel 16 without altering its electron structure to form such chemical bonds.

Passivation layer 50 may be composed of any suitable silylating agents. For example, passivation layer 50 may be made of a compound with chemical formulae $X_3SiRSiX_3$, where X is a halide and R is a hydrocarbyl group (e.g., —$CH_2$—, —$CH_2CH_2$—, or —$CH_2CH_2CH_2$—, etc.). The halide may be fluorine, chlorine, or bromine. Other examples of possible silylating agents for forming passivation layer 50 include compounds with formulae $X_{3-y}R_ySiR'SiRyX_{3-y}$ and $SiX_{4-y}R_y$, where y is 0, 1, or 2, X is a surface reactive group (e.g., halides, alkoxides, esters, hydroxyls, and hydrides), and R and R' are hydrocarbyl or halocarbyl (e.g., fluorocarbyl) groups. Other silylating agents may also be cyclic or acyclic compounds of silicon such as those containing Si—N—Si or Si—O—Si linking groups and terminal groups containing some surface reactive functional groups (X) and other groups for chemically selective passivation (R, R').

Channel 16 may have one or more imagers for gathering image data on the sample. At the end of each channel 16, the sample may be collected in reservoir 18 and evaluated in the reservoir. Alternatively, the sample may be transported to a different chamber for evaluation.

Figure 2:
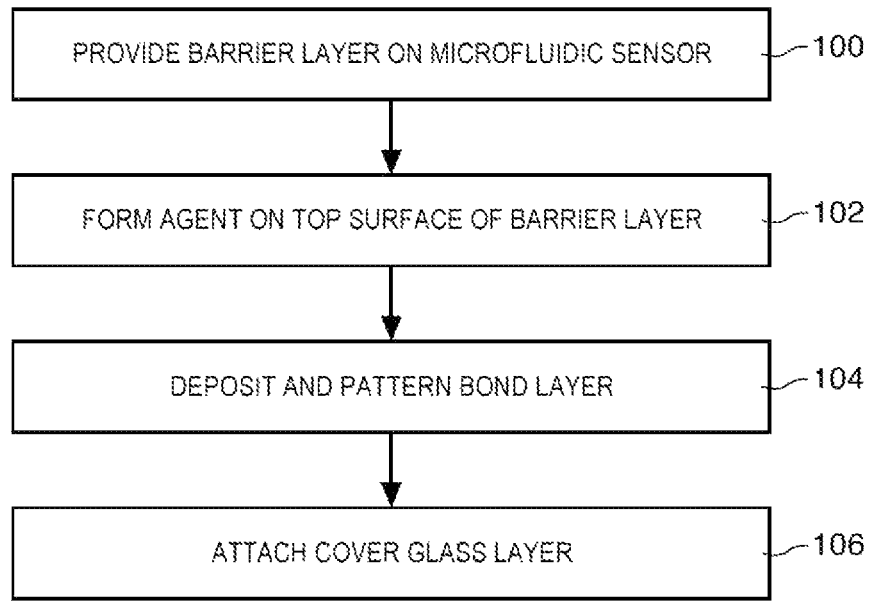
FIG. 2 is a flow chart of illustrative steps involved in forming a system of the type shown in FIG. 1 in accordance with an embodiment of the present invention.

Illustrative steps that may be involved in forming a channel (such as channel 16) having a protective passivation layer (such as layer 50) for a sensor (such as sensor 12) are shown in FIG. 2.

At step 100, a barrier layer such as barrier layer 52 may be formed on a top surface of a sensor (e.g., on a top surface of integrated circuit substrate 34).

At step 102, a protective coating such as passivation layer 50 (e.g., base-resistant agent or other agent) may be formed on barrier layer 52. Passivation layer 50 may be applied over barrier layer 52 such that it protects barrier layer 52 and integrated circuit 34 from damage by materials to be introduced into a channel over integrated circuit substrate 34. As examples, passivation layer 50 may be a base-resistant coating applied by low-temperature vapor deposition or liquid phase deposition to coat substantially all of a barrier layer that is formed over substrate 34.

At step 104, a bond layer such as bond layer 40 may be deposited on passivation layer 50. The bond layer may then be patterned to form standoffs for cover glass layer 28.

At step 106, a cover layer such as cover glass 28 may be attached to remaining portions of the patterned bond layer so that the cover layer, portions of the bond layer, and the protective layer of substrate 34 form the surfaces of a fluid channel over image pixels 36.

Steps 102, 104, and 106 may be performed at a wafer level (e.g., barrier layer 52, bond layer 40, and glass layer 28 may be formed over a wafer having multiple image sensor integrated circuits and then diced into individual microfluidic systems) or at a die level (e.g., barrier layer 52, bond layer 40, and glass layer 28 for an individual microfluidic system may be formed on an image sensor integrated circuit die that has already been cut from a wafer).

The steps described above in connection with FIG. 2 are merely illustrative. If desired, other methods may be used to form a fluid channel for a microfluidic system with a protective layer that prevents damage to the system from fluids and reactants.

Figure 3:
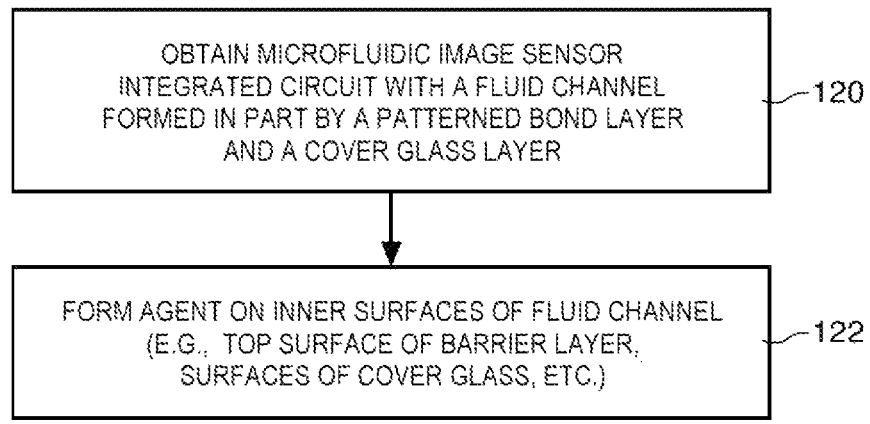
FIG. 3 is a flow chart of illustrative steps involved in forming a system of the type shown in FIG. 1 in accordance with an embodiment of the present invention.

For example, another set of illustrative steps that may be used in forming channel 16 are shown in FIG. 3.

At step 120, an image sensor integrated circuit having a fluid channel formed from a portion of an image sensor integrated circuit, a portion of a patterned bond layer and a portion of a cover glass layer may be obtained. Obtaining the image sensor integrated circuit with the fluid channel may include obtaining an image sensor integrated circuit, depositing and patterning a bond layer on the integrated circuit and attaching a cover glass layer to the patterned bond layer. If desired, the obtained image sensor integrated circuit may include a barrier layer over the surface of the integrated circuit.

At step 122, a layer of protective material such as passivation layer 50 (e.g., a base-resistant agent or other agent) may be formed on the inner surfaces of the fluid channel (e.g., on the top surface of a barrier layer over the integrated circuit such as barrier layer 52, on some or all surfaces of bond layer 40 and some or all surfaces of cover glass 28 as shown in FIG. 1). Passivation layer 50 may be applied over barrier layer 52, bond layer 40, and portions of cover glass layer 28, such that the applied coating protects the surfaces of integrated circuit 34, glass layer 28, and bond layer 40 from damage by materials to be introduced into the fluid channel over integrated circuit substrate 34. Applying passivation layer 50 may include applying a base-resistant coating using low-temperature vapor deposition techniques and/or liquid phase deposition techniques (as examples).

Figure 4:
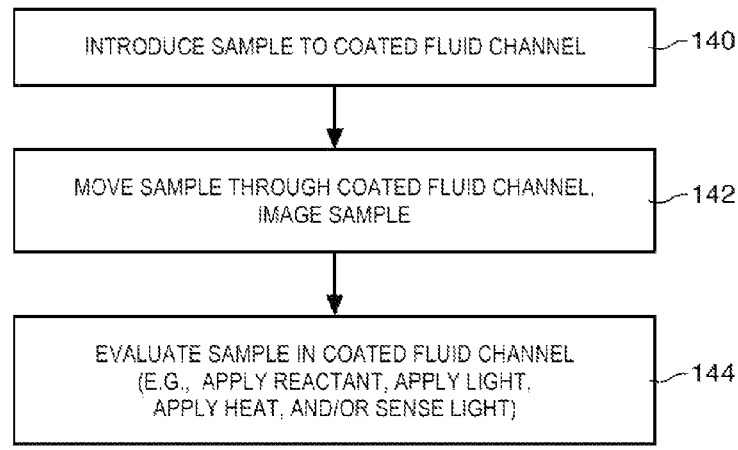
FIG. 4 is a flow chart of illustrative steps involved in using a system with coated fluid channels to evaluate samples in accordance with an embodiment of the present invention.

Illustrative steps that may be involved in using system 10 to evaluate samples are shown in FIG. 4.

At step 140, a sample of fluid such as a fluid containing a fluorescent sample or other particles may be introduced into a coated fluid channel such as channel 16 of FIG. 1. For example, a sample may be introduced in entrance port 24 by fluid source 14.

At step 142, the flow of the sample through channel 16 may be controlled using flow control structures to route the sample through the coated fluid channel.

At step 144, the sample may be evaluated within channel 16 of system 10. For example, reactant such as reactant 44 within the channel may react with the sample. One or more light sources such as light source 32 may be used to illuminate cells or other specimens in the fluid. The illumination may be provided in the form of white light or one or more different colors of light. Heaters may be used to adjust the temperature of the sample during evaluation. The sample may be imaged by the image pixels on integrated circuit substrate 34 at this step. The amount of light in channel 16 may be evaluated using sensor pixels 36. For example, following illumination with a light source, sensor pixels 60 may be used to detect fluorescence signals. A checkerboard pattern or other tiled pattern may be used for color filters 53, sensor pixels 36, and/or reactant within the channel to allow information on the response of the sample to different colors and/or reactants to be measured. The data that is gathered during step 144 may be gathered and processed using control circuitry 42 (as an example).

Figure 5:
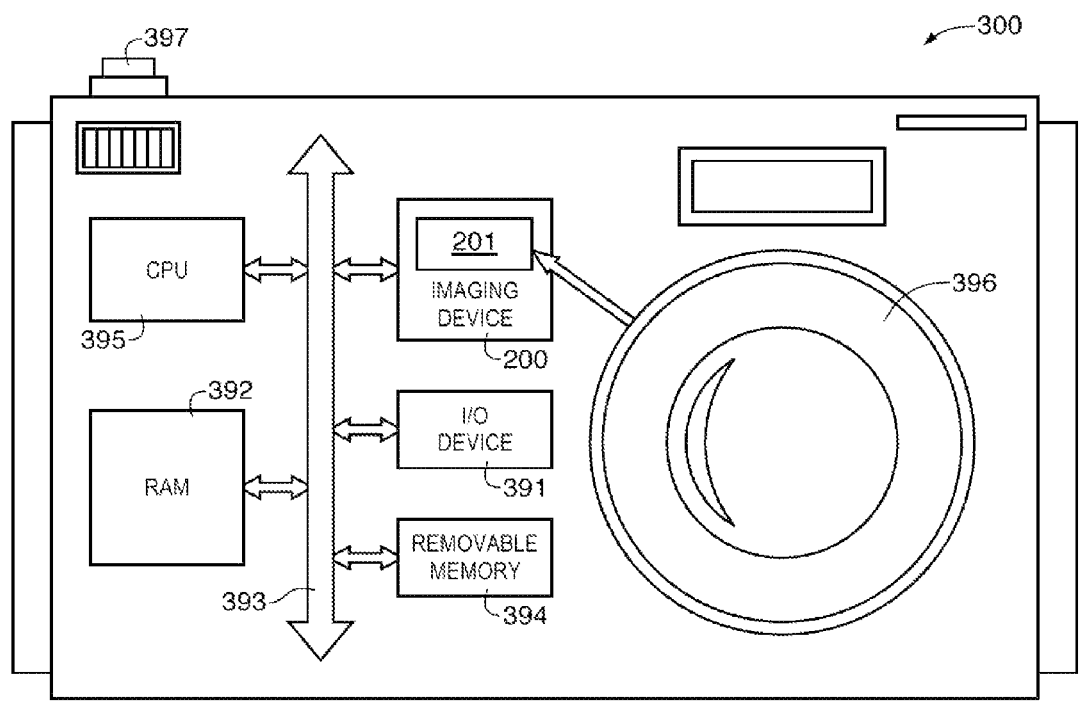
FIG. 5 is a block diagram of an imager employing the embodiment of FIG. 1 in accordance with an embodiment of the present invention.

FIG. 5 shows in simplified form a typical processor system 300, such as a digital camera, which includes an imaging device 200. Imaging device 200 may include an opto-fluidic system such as system 10 of FIG. 1 having an array 201 of image pixels 36. Processor system 300 is exemplary of a system having digital circuits that may include imaging device 200. Without being limiting, such a system may include a computer system, still or video camera system, scanner, machine vision, vehicle navigation, video phone, surveillance system, auto focus system, star tracker system, motion detection system, image stabilization system, and other systems employing an imaging device.

Processor system 300, which may be a digital still or video camera system, may include a lens such as lens 396 for focusing an image onto a pixel array such as pixel array 201 when shutter release button 397 is pressed. Processor system 300 may include a central processing unit such as central processing unit (CPU) 395. CPU 395 may be a microprocessor that controls camera functions and one or more image flow functions and communicates with one or more input/output (I/O) devices 391 over a bus such as bus 393. Imaging device 200 may also communicate with CPU 395 over bus 393. System 300 may include random access memory (RAM) 392 and removable memory 394. Removable memory 394 may include flash memory that communicates with CPU 395 over bus 393. Imaging device 200 may be combined with CPU 395, with or without memory storage, on a single integrated circuit or on a different chip. Although bus 393 is illustrated as a single bus, it may be one or more buses or bridges or other communication paths used to interconnect the system components.

Various embodiments have been described illustrating apparatus for imaging and evaluating samples of fluids containing samples and other materials. An integrated circuit such as an image sensor array integrated circuit may be provided with fluid channels having a protective coating. Sets of image sensor pixels from an image sensor array on the integrated circuit may form imagers in the fluid channels. A sample may be introduced into a channel for imaging by the imagers and for evaluation using other sample evaluation structures.

Portions of the channels such as widened chambers may be provided for adding diluent and other reactants such as dyes, antigens, antibodies, chemical compounds, and other materials to the sample fluid. The protective coating may be a passivation layer formed on one or more surfaces of the fluid channel that protects components of the apparatus from damage from the sample fluid, the diluent, and other reactants. The protective coating may be a base-resistant material such as a silylating agent. A barrier layer may be formed in between the protective coating and the imager. A bond layer may be formed and patterned above the protective coating to form a portion of the channel. A cover glass layer may be attached to portions of the bond layer to form a top portion of the channel. The protective coating may be formed over the inner surfaces of the channel including on some or all of the surfaces of the cover glass.

The foregoing is merely illustrative of the principles of this invention which can be practiced in other embodiments.

What is claimed is:

1. Apparatus, comprising:
    an image sensor integrated circuit containing image sensor pixels that form at least one imager;
    a fluid channel on the image sensor integrated circuit that is configured to receive a sample containing fluid, wherein the at least one imager is located in the channel;
    a protective coating on at least one surface of the fluid channel; and
    a barrier layer between the protective coating and image sensor integrated circuit, the barrier layer comprising a transparent material.

2. The apparatus defined in claim 1, further comprising:
    a bond layer, wherein the bond layer forms portions of sidewalls of the fluid channel.

3. The apparatus defined in claim 2, further comprising a cover glass layer.

4. The apparatus defined in claim 3, wherein a portion of the protective coating is formed on at least one surface of the cover glass layer.

5. The apparatus defined in claim 4, wherein an additional portion of the protective coating is formed on a bottom surface of the fluid channel.

6. The apparatus defined in claim 1, wherein the protective coating comprises a base-resistant silylating material.

7. The apparatus defined in claim 1, wherein the protective coating comprises a fluorocarbyl material.

8. The apparatus defined in claim 1, further comprising a reactant, wherein the protective coating is interposed between the reactant and the image sensor integrated circuit.

9. The apparatus defined in claim 1, wherein the at least one imager is configured to capture images of biological specimens in the sample containing fluid.

10. The apparatus defined in claim 1, wherein the protective layer is chemically bonded to the at least one surface of the fluid channel.

11. The apparatus defined in claim 1, wherein the protective layer is physically bonded to the at least one surface of the fluid channel.

12. A method of forming a microfluidic system, the method comprising:
    obtaining an image sensor integrated circuit having a plurality of image sensor pixels, wherein the plurality of image sensor pixels are formed at a surface of the image sensor integrated circuit that forms a portion of a fluid channel;
    forming a barrier layer on the surface of the obtained image sensor integrated circuit, the barrier layer comprising a transparent material; and
    forming a protective layer over the barrier layer, wherein the protective layer protects portions of the microfluidic system from substances in a fluid to be introduced into the fluid channel.

13. The method defined in claim 12, further comprising:
    depositing a bond layer on the protective layer; and
    patterning the bond layer to form sidewalls of the fluid channel.

14. The method defined in claim 13, further comprising:
    attaching a cover glass layer to the patterned bond layer.

15. The method defined in claim 12 wherein obtaining the image sensor integrated circuit having the plurality of image sensor pixels comprises obtaining a microfluidic image sensor integrated circuit having a patterned bond layer and a cover glass layer, and wherein the patterned bond layer and the cover glass layer form additional portions of the fluid channel.

16. The method defined in claim 15 wherein forming the protective layer over the surface of the obtained image sensor integrated circuit comprises forming the protective layer on the additional portions of the fluid channel.

17. The method defined in claim 12 wherein forming the protective layer over the surface of the obtained image sensor integrated circuit comprises forming a silylating agent over the surface of the obtained image sensor integrated circuit.

18. A system, comprising:
    a central processing unit;
    memory;
    input-output circuitry; and
    an imaging device, wherein the imaging device comprises:
    a pixel array having a plurality of imaging pixels;
    a fluid channel on the pixel array that is configured to receive a sample containing fluid, wherein the pixel array is located in the channel;
    a protective coating on at least one surface of the fluid channel; and a barrier layer between the protective coating and image sensor integrated circuit, the barrier layer comprising a transparent material.

* * * * *